US008675450B2

(12) United States Patent
Tran et al.

(10) Patent No.: US 8,675,450 B2
(45) Date of Patent: Mar. 18, 2014

(54) DISPLACEMENT ESTIMATING METHOD AND DISPLACEMENT ESTIMATING APPARATUS

(75) Inventors: Anh Tuan Tran, Singapore (SG); Kok Seng Chong, Singapore (SG); Shu Feng Fan, Singapore (SG)

(73) Assignee: Panasonic Corporation, Osaka (JP)

( * ) Notice: Subject to any disclaimer, the term of this patent is extended or adjusted under 35 U.S.C. 154(b) by 344 days.

(21) Appl. No.: 13/256,642

(22) PCT Filed: Jan. 19, 2011

(86) PCT No.: PCT/JP2011/000259
§ 371 (c)(1),
(2), (4) Date: Sep. 15, 2011

(87) PCT Pub. No.: WO2011/089898
PCT Pub. Date: Jul. 28, 2011

(65) Prior Publication Data
US 2012/0002506 A1    Jan. 5, 2012

(30) Foreign Application Priority Data

Jan. 20, 2010  (JP) ................................. 2010-010336

(51) Int. Cl.
*G01S 15/00* (2006.01)
*G06K 9/00* (2006.01)
(52) U.S. Cl.
USPC ............................................ 367/99; 382/131
(58) Field of Classification Search
USPC ..................... 382/131; 367/99, 100
See application file for complete search history.

(56) References Cited

U.S. PATENT DOCUMENTS

| 6,270,459 | B1 | 8/2001 | Konofagou et al. |
| 6,277,074 | B1 | 8/2001 | Chaturvedi et al. |
| 6,506,158 | B2 | 1/2003 | Kawagishi et al. |
| 6,813,315 | B1 * | 11/2004 | Auyeung et al. ......... 375/240.16 |
| 7,993,272 | B2 * | 8/2011 | Chomas et al. ............... 600/437 |
| 2001/0034485 | A1 | 10/2001 | Kawagishi et al. |

(Continued)

FOREIGN PATENT DOCUMENTS

| JP | 2003-180686 | 7/2003 |
| JP | 2007-029703 | 2/2007 |

(Continued)

OTHER PUBLICATIONS

International Search Report issued Apr. 5, 2011 in International (PCT) Application No. PCT/JP2011/000259.

(Continued)

*Primary Examiner* — Isam Alsomiri
*Assistant Examiner* — Hovhannes Baghdasaryan
(74) *Attorney, Agent, or Firm* — Wenderoth, Lind & Ponack, LLP.

(57) ABSTRACT

Disclosed is a displacement estimating method of iteratively estimating displacement using ultrasound signals, and the method includes: transmitting, to a medium, at least one of the ultrasound signals to scan the medium; receiving the ultrasound signal reflected from the scanned medium; calculating a size of a window; calculating a border of the window based on the calculated window size; estimating displacement for each depth of the ultrasound signal, using the window with the calculated border; warping the ultrasound signal based on the estimated displacement; and guiding convergence of the method using the warped ultrasound signal so that a correlation value of the ultrasound signal is larger.

9 Claims, 13 Drawing Sheets

(56) References Cited

U.S. PATENT DOCUMENTS

| | | | |
|---|---|---|---|
| 2004/0034304 A1 | 2/2004 | Sumi | |
| 2005/0259877 A1* | 11/2005 | Wang et al. | 382/236 |
| 2006/0047462 A1* | 3/2006 | Picciotto et al. | 702/120 |
| 2006/0173319 A1 | 8/2006 | Sumi | |
| 2006/0184020 A1 | 8/2006 | Sumi | |
| 2006/0184025 A1 | 8/2006 | Sumi | |
| 2007/0038101 A1 | 2/2007 | Yoon et al. | |
| 2008/0019609 A1 | 1/2008 | Hamilton et al. | |
| 2009/0221916 A1 | 9/2009 | Konofagou et al. | |
| 2009/0318811 A1 | 12/2009 | Yoon et al. | |
| 2009/0324040 A1 | 12/2009 | Lindop et al. | |
| 2010/0016721 A1 | 1/2010 | Kanai et al. | |

FOREIGN PATENT DOCUMENTS

| | | |
|---|---|---|
| JP | 2007-152074 | 6/2007 |
| JP | 2009-537273 | 10/2009 |
| WO | 2007/135450 | 11/2007 |
| WO | 2008/038615 | 4/2008 |

OTHER PUBLICATIONS

C. Sumi et al., "Improvement of the Measurement Accuracy of the Local Tissue Displacement by Making a Local Region Smaller During the Iterative RF-Echo Phase Matching", J Med Ultrasonics, vol. 24, No. 3, 1997 with partial English translation.

C. Sumi, "Fine Elasticity Imaging Utilizing the Interative RF-echo Phase Matching Method", IEEE Trans. On UFFC., vol. 46, No. 1, Jan. 1999.

C. Sumi et al., "Measurement of Displacement Vector Field Using the Phase of 2D Cross Spectral", The Japan Society of Ultrasonics in Medicine, vol. 21, 1994 with partial English translation.

C. Pellot-Barakat et al., "Ultrasound Elastography Based on Multiscale Estimations of Regularized Displacement Fields", IEEE Trans. Med. Imaging, vol. 23, No. 2. Feb. 2004.

* cited by examiner

DISPLACEMENT ESTIMATING METHOD AND DISPLACEMENT ESTIMATING APPARATUS

TECHNICAL FIELD

The present invention introduces a method to estimate displacements using ultrasound signals. It can be used in applications requiring estimation of displacements, either as the final results or as the intermediate step for further processing. It can be deployed in medical and industrial ultrasound machines.

BACKGROUND ART

Ultrasound devices work on the basis of non-invasive transmission and reception of high frequency mechanical sonic waves.

The transducers of such devices transmit the ultrasound waves to the medium under scan.

The waves interact with the underlying structures in the medium, through scattering and reflections.

The underlying structures include, for example, a structure inside the medium rather than the surface thereof. The underlying structures include, for example, blood vessel in the human body.

The scattered and reflected waves contain the useful information of the underlying structures, which are received by the transducers and processed by the ultrasound devices to be presented to users.

FIG. 8 illustrates ultrasound RF signals.

One of the most basic types of data that an ultrasound device obtains from the reflected waves is Radiofrequency Signal (RF) signals (FIG. 8).

It is the direct translation of the received waves from their analog form to their digital form.

From ultrasound RF signals, other types of data can be derived, such as brightness mode (B-mode) images, Doppler images, etc. with different applications.

One of many applications is to analyze the motions of the underlying structures in the scanned medium.

The Doppler Effect is utilized as a simple method to deduce the direction and strength of structural motion.

However, the Doppler Effect has very limited accuracy.

For applications such as monitoring of blood flow in medical ultrasound, wherein the accuracy is not strictly required, Doppler ultrasound is suitable.

However, for applications which require a much higher level of accuracy, wherein the structures are small and their movement is minuscule, a much more sensitive technique is demanded.

Recently, ultrasound elastography is a new application wherein structure's displacements can be used to deduce the structure's elasticity.

These displacements need to be accurately estimated from the received ultrasound signals to provide an accurate estimation of elasticity.

Apart from resolution (i.e. the ability to estimate minuscule displacements), a higher level of accuracy is also required for displacement estimation using ultrasound.

In many prior arts, displacements are estimated from ultrasound B-mode images.

However, the quality of the estimated displacements depends largely on the quality and the resolution of the B-mode images.

For most ultrasound devices, the resolution of B-mode images does not allow displacements of micrometer order to be estimated.

Some other works focus on estimating displacements directly from the received RF signals.

Cross-correlation is one of the most common techniques, as in [1].

However, cross-correlation is computationally intensive, and it can only estimate displacements corresponding to multiple of sampling points.

Displacements of micrometer order usually correspond to a small fraction of one sampling interval.

Thus, the cross-correlation fails to estimate the displacements.

There are works which rely on signal interpolation to estimate displacements in such situation.

However, this will increase the processing time, and the estimation quality depends on the interpolation method.

Auto-correlation relies on the phase information of the quadrature demodulated signals (a.k.a. base-band signals) of the received RF signals.

This method has the advantage of being able to estimate displacement corresponding to sub-sample of RF signals, which is described in [2].

However, it is highly prone to noise, and it's affected by amplitude modulation effect.

More specifically, the estimated displacements are biased toward the region with high signal power.

To overcome the effect of noise, a larger set of samples can be chosen to perform auto-correlation, which reduces the ability to estimate more detailed displacements.

Some methods are developed to overcome the inaccuracy of the estimated displacements from the above techniques.

'Coarse to fine' approach makes use of different windowing regions for different stage of estimation, so that the first stage provides a coarse estimation of displacement, and the second stage gives a finer estimation to improve the accuracy, as in [3].

However, no method for evaluating estimation quality is available.

In some other works, signal warping based on the estimation result of the first stage is used to improve the accuracy of this result by conducting a second estimation stage, and combine the results, as in [1].

Other displacement correcting methods are also available as in [2].

These methods carry a high risk of divergence; hence the number of stages has to be constrained.

In addition, there are no methods to guide the convergence, and to overcome the effect of noise and bias caused by uneven distribution of RF signal power.

An improvement to these methods is needed, to give a more comprehensive iterative estimation method, which provides an indication of displacement estimation quality, guides the convergence of the iterative estimation without having to limit the number of estimation stages, and gives a high accuracy even for minuscule displacements.

The techniques disclosed in Patent Literatures 1 to 6 are known as the conventional examples.

CITATION LIST

Patent Literature

[PTL 1] U.S. Pat. No. 6,277,074
[PTL 2] U.S. Pat. No. 6,506,158 (US Patent Application No. 2001/0034485)

[PTL 3] US Patent Application No. 2008/0019609
[PTL 4] US Patent Application No. 2009/0221916
[PTL 5] U.S. Pat. No. 6,270,459
[PTL 6] International Publication WO2008/038615

SUMMARY OF INVENTION

Technical Problem

The current single-stage displacement estimation methods have the problems in the accuracy and displacement resolution.

Cross-correlation based methods are not able to estimate small displacements which correspond to sub-sampling interval without signal interpolation.

Nevertheless, they are less affected by noise.

Thus, cross-correlation based methods have higher accuracy, but lower displacement resolution.

In order to improve the displacement resolution of cross-correlation methods, signal interpolation can be applied.

However, it increases the processing power considerably if the displacements to be estimated are of micrometer orders.

Moreover, the accuracy of this method depends on the quality of interpolation algorithms.

Auto-correlation based methods are able to estimate small displacements, but they are highly prone to noise.

Thus, they have a higher displacement resolution, but lower accuracy.

Two-stage estimation methods are available to improve the accuracy.

However, the problems in these methods lie in three aspects: lack of comprehensive iterative approach, lack of a method for evaluating displacement quality, and lack of a solution for factors that limit the accuracy of displacement, i.e. noise and amplitude modulation effect.

The comprehensive iterative approach should incorporate the techniques to guide the convergence of the iterative estimation.

The object of the present invention includes providing a displacement estimating apparatus (displacement estimating method) that can estimate tissue displacement with high accuracy and that provides information appropriate for differentiating benign tumors from malignant ones, or normal tissue, based on the estimated displacement.

The other object of the present invention includes providing a displacement estimating apparatus that can guide the convergence of the iterative displacement estimating processes, with a small number of iterations and high accuracy.

Solution to Problem

In order to solve the problems, a displacement estimating method according to an aspect of the present invention is a displacement estimating method of iteratively estimating displacement using ultrasound signals, and includes: transmitting, to a medium, at least one of the ultrasound signals to scan the medium; receiving the ultrasound signal reflected from the scanned medium; calculating a size of a window; calculating a border of the window based on the calculated window size; estimating displacement for each depth of the ultrasound signal, using the window with the calculated border; warping the ultrasound signal based on the estimated displacement; and guiding convergence of the method using the warped ultrasound signal so that a correlation value of the ultrasound signal is larger.

In this invention, the inventors teach a method to estimate displacements using ultrasound using iterative estimation approach.

According to the inventors' experiments, if the estimation window size is kept the same or not configured properly for all iterative estimation rounds, the estimated displacements do not converge.

So a window calculation method is introduced to help this convergence.

The window calculation method comprises two parts: a window size calculation for guiding the convergence of the iterative estimation, and a window border calculation to overcome the effects of noise and bias caused by uneven distribution of signal power.

The window size calculation decides the window size differently for each round of iterative estimation.

This calculation has two purposes: to obtain a more detailed estimation result in the subsequent rounds, and to ensure the convergence of the estimation.

In other words, it is possible to prevent a case where the convergence cannot be achieved and no accurate displacement amount can be obtained with processing using an inappropriate window size. Furthermore, it is possible to reliably obtain the convergence and a more accurate displacement amount, with processing using an appropriate window size.

The window border calculation makes use of signal power to decide the borders of the estimation window at each estimation location.

In the conventional estimation method, the windows are usually symmetrical with respect to the location.

This is one of the reasons for the bias caused by uneven signal power distribution.

Using signal power to decide the window borders overcomes such effect.

The assessment of the quality of the estimated displacement is introduced to further guide the convergence, to ensure that the iterative estimation method always converges to the best result.

The accuracy of displacement estimation is ensured using a comprehensive iterative approach according to the present invention including a method to guide the convergence, a method to overcome factors that limit accuracy, and a method to evaluate the quality of results.

Advantageous Effects of Invention

FIG. 10 illustrates the improvement in displacement estimation after applying backtracking algorithm in simulation.

FIG. 11 illustrates the same improvement in a phantom experiment.

is FIG. 10 shows that the estimated displacement in the first round of estimation (displacement 1001) deviates from the simulated displacement profile (profile 1000).

However, at the final round of the backtracking algorithm with windowing schemes to guide the convergence, the estimated displacement (displacement 1002) matches closely with the simulated profile.

FIG. 11 shows the estimation results from the phantom experiment in which the global displacement is generated.

A single line is chosen for illustration (see profile 1100).

Because the global displacement is generated, a constant displacement profile (profile 1101) is expected.

For the first round of estimation, the result (see data 1102) does not match well with the expected displacement.

However, the estimation result in the final round (see data 1103) has a much better representation of a global movement than that of the first round.

Furthermore, a displacement estimating apparatus that can perform processing with an appropriate window size can be provided.

The object of the present invention includes providing a displacement estimating apparatus (displacement estimating method) that can estimate tissue displacement with high accuracy and that provides information appropriate for differentiating benign tumors from malignant ones, or normal tissue, based on the estimated displacement.

The other object of the present invention includes providing a displacement estimating apparatus that can guide the convergence of the iterative displacement estimating processes, with a small number of iterations and high accuracy.

DESCRIPTION OF EMBODIMENTS

Hereinafter, embodiments will be described with reference to drawings.

Figure 12:
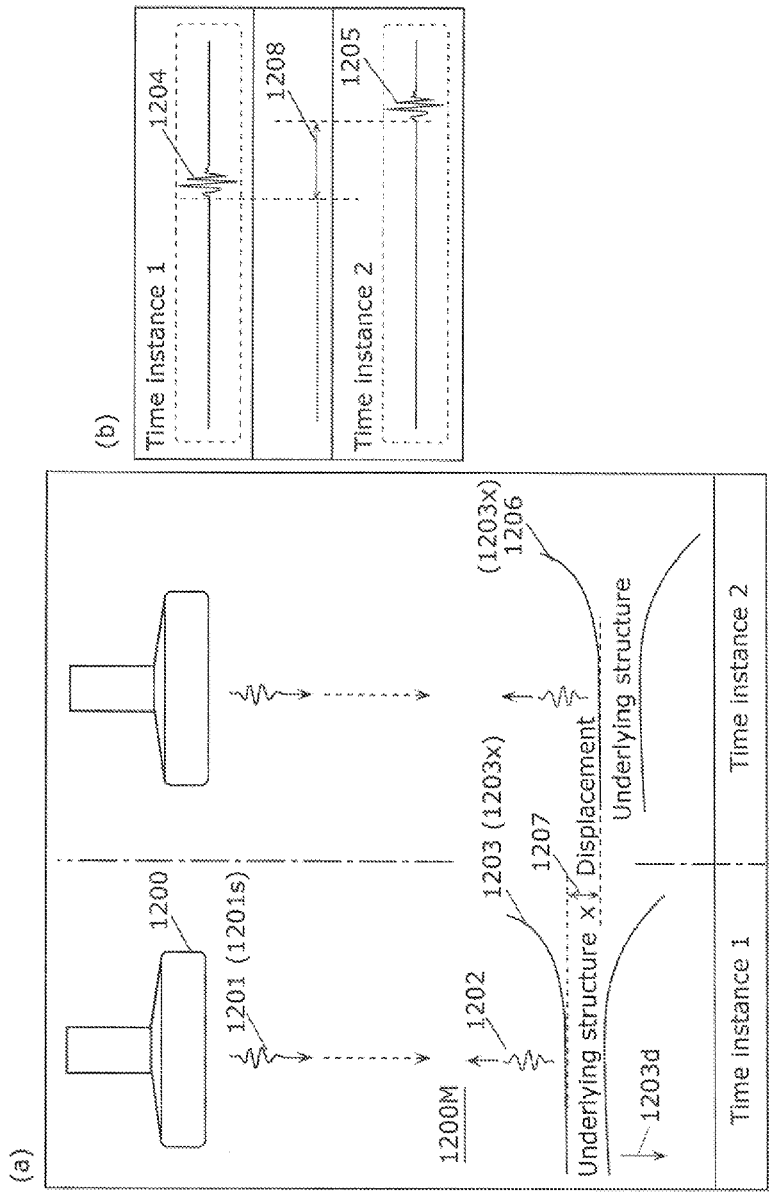
FIG. 12 illustrates displacements of underlying structure and effects on RF signals.
Figure 13:
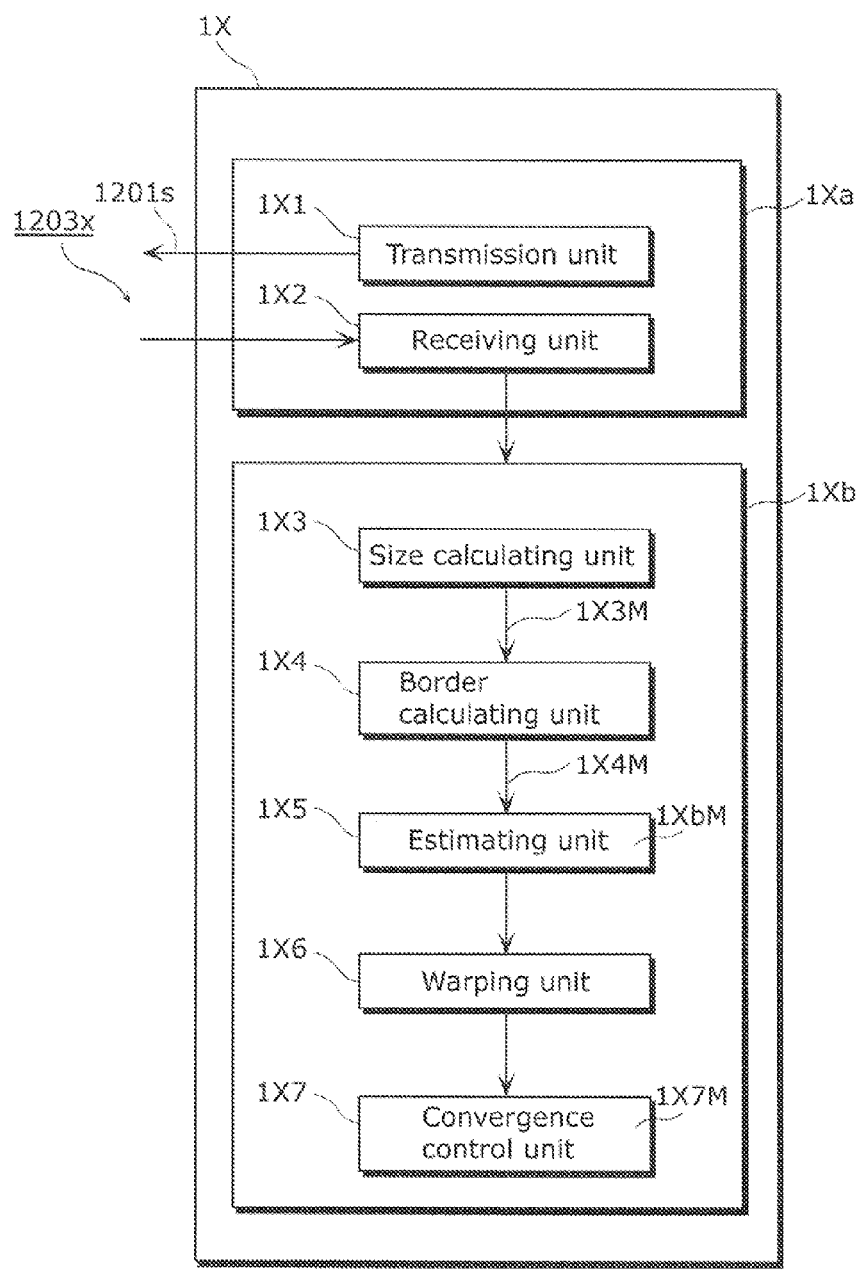
FIG. 13 illustrates a block diagram of a displacement estimating apparatus.

The displacement estimating method (a displacement estimating apparatus 1X in FIG. 13) according to an embodiment is a method of iteratively estimating displacement (displacement 1207 in FIG. 12) using ultrasound signals (ultrasound signal 1201s in FIG. 13).

In other words, for example, iterations of identifying the size of displacement and iterations of specific processing enable identification of the size of the displacement with relatively high accuracy.

A transmission unit 1X1 in an ultrasound processing unit 1Xa in FIG. 13 transmits at least one of the ultrasound signals to a medium (a medium 1200M (FIG. 12) and an underlying structure (object to be measured for displacement) 1203x (see FIGS. 12 and 13)) to scan the medium.

In other words, ultrasound signals are transmitted to positions in a line direction (direction 81L in FIG. 8), and scanning is performed at the positions.

Then, a receiving unit 1X2 receives the ultrasound signal (ultrasound signal 1201s) reflected from the scanned medium.

The ultrasound processing unit 1Xa is, for example, a probe.

Figure 3:
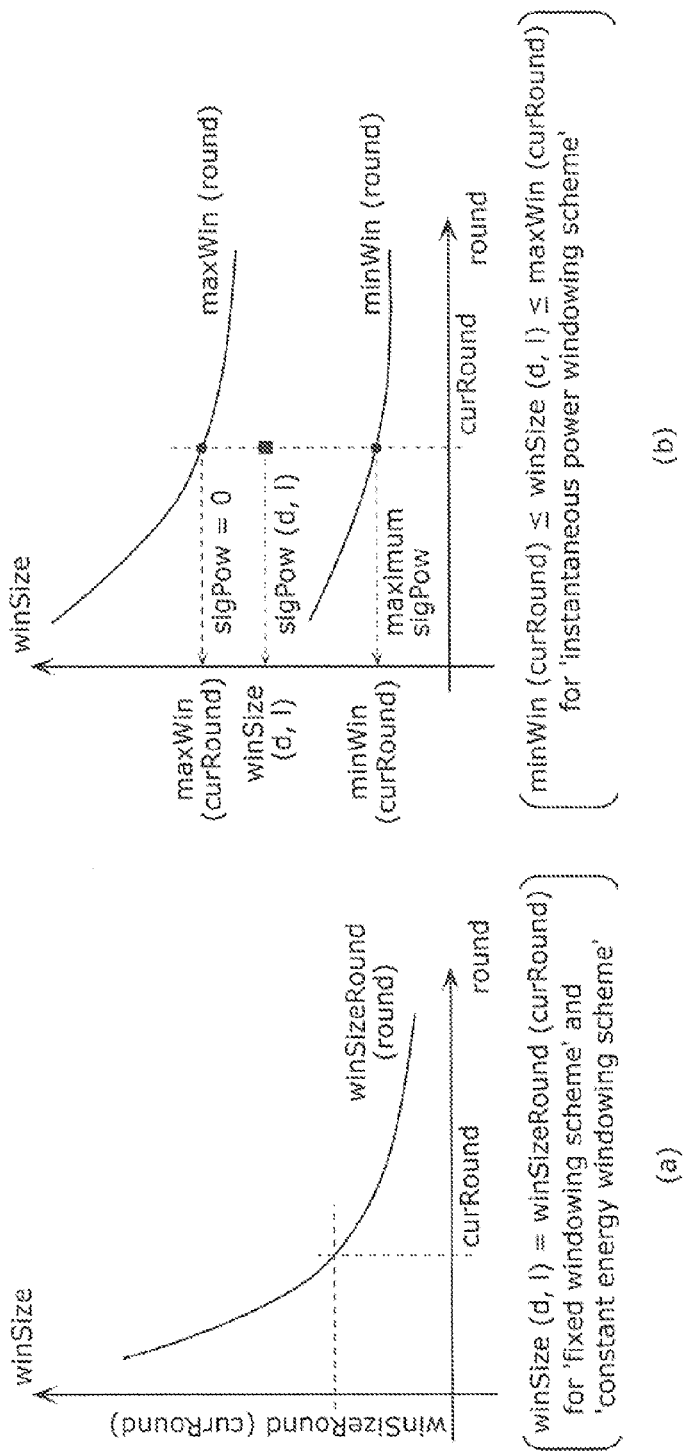
FIG. 3 illustrates an example of window size calculation.

Then, a size calculating unit 1X3 included in an information processing unit 1Xb in FIG. 13 calculates a window size (window size 1X3M in FIG. 13, for example, winSize in (a) and (b) of FIG. 3).

In other words, the window size of each° round is determined.

The size calculating unit 1X3 may include, for example, a window calculating unit 102 (FIG. 1) and at least part of the window calculating unit 102.

In other words, the window size for the n-th round is determined, for example, based on a correlation value for a (n−1)th round (a correlation value 1X7M in FIG. 13) (n≥2).

Figure 4:
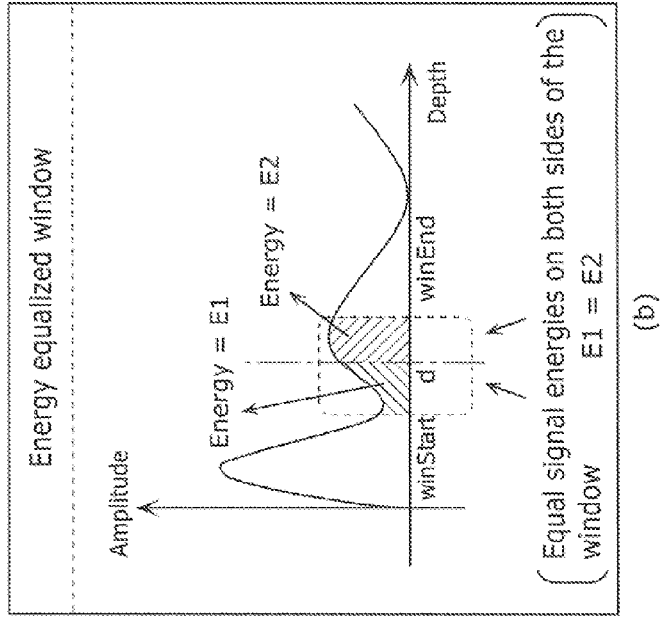
FIG. 4 illustrates an example of a symmetrical window and an energy equalized window.
Figure 4:
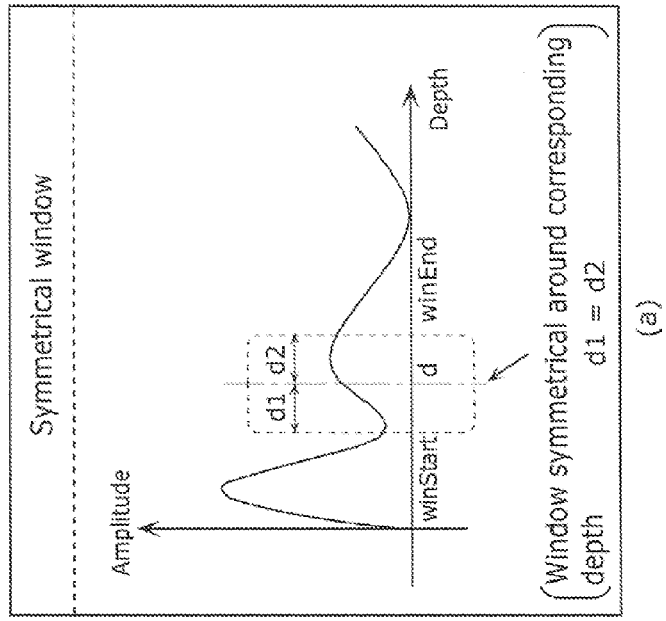

A border calculating unit 1X4 calculates the borders of a window (border information 1X4M, see a starting end of a window (winStart) and a terminal end (winEnd) in (a) and (b) of FIG. 4) based on the calculated window size.

Figure 1:
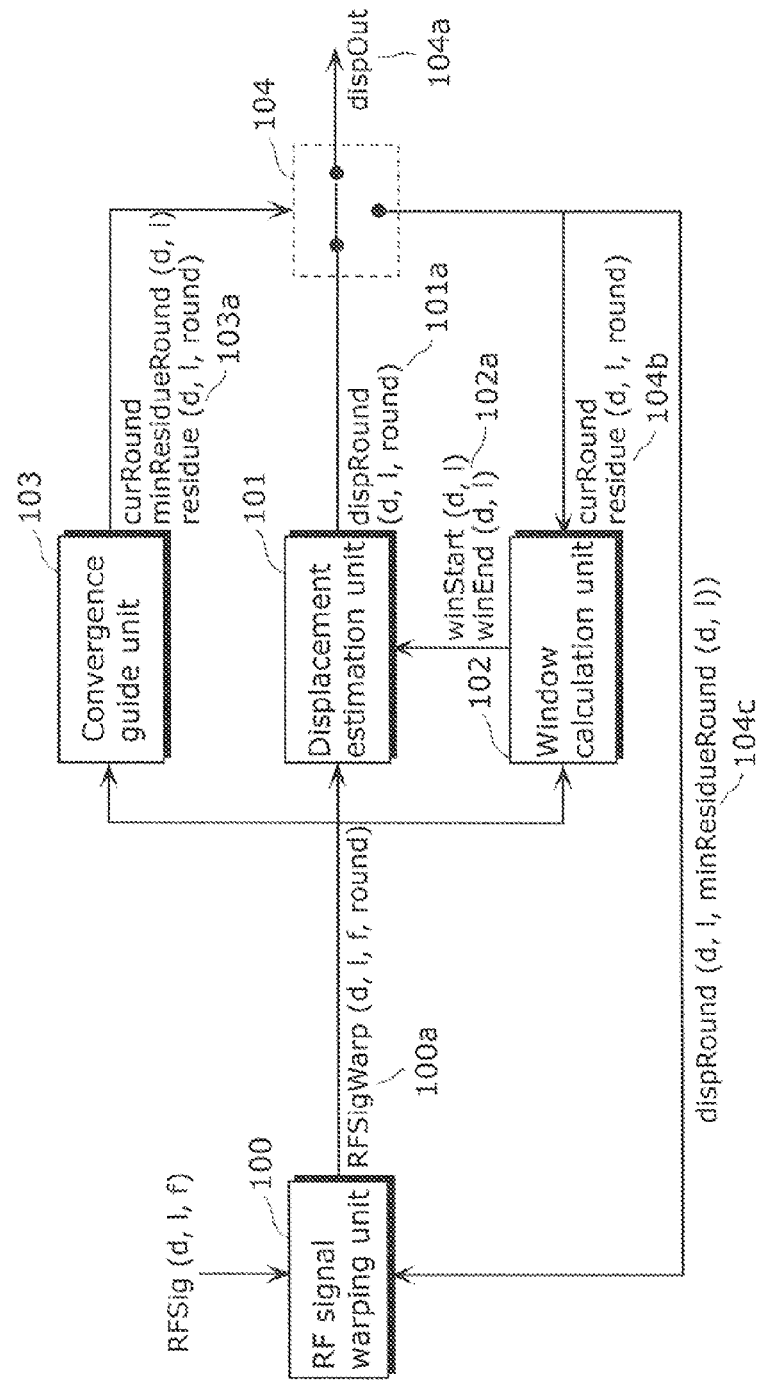
FIG. 1 illustrates a displacement estimation method according to the present invention.

The border calculating unit 1X4 may be, for example, at least a part of the window calculating unit 102 (FIG. 1).

In other words, the starting end and the terminal end are determined such that a width therebetween is the calculated window size.

An estimating unit 1X5 estimates the displacement (displacement 1XbM) at a depth of each of the ultrasound signals using the window with the calculated border.

The estimating unit 1X5 may be, for example, at least a part of a displacement estimating unit 101 (FIG. 1).

In other words, displacements at positions having different distances from the displacement estimating apparatus are identified.

Then, a warping unit 1X6 warps the ultrasound signal based on the estimated displacement.

The warping unit 1X6 may be, for example, at least a part of an RF signal warping unit 100 (FIG. 1).

A convergence control unit 1X7 guides the convergence of the displacement estimating method using the warped ultrasound signal so that the correlation value of the ultrasound signal (the correlation value 1X7M) is increased.

The convergence control unit 1X7 may be, for example, at least a part of a convergence guiding unit 103.

In other words, the size of displacement estimated at a round in which the correlation value calculated using the warped ultrasound signal is the largest is identified as the size of the displacement with the highest accuracy.

Then, the calculated window size is varied so that the window size to be used for consecutive rounds is gradually decreased.

In other words, the window size calculated at each of the rounds is smaller than the window size calculated at the previous round, and the window size to be calculated is changed to the smaller size.

Then, the window size is calculated so that signal energies in all windows (depths) are equal.

As the correlation value of the ultrasound signal (correlation value at the (n−1)th round) is larger, the window size (the window size at the n-th round) is calculated to be smaller. The relationship between a window size and an evaluation value of a convergence degree at each round, such as a correlation value can be determined using a predetermined relational expression based on values of biomedical experiments, or with reference to a table indicating the association between the window sizes and the evaluation values.

Then, the window size in association with the correlation value at the (n−1)th round is determined as the window size of the n-th round.

More specifically, the displacement estimating apparatus performs the next operations, for example.

An ultrasound signal 1201s may be transmitted to an underlying structure 1203x (FIG. 12) that is an object to be measured (for example, malignant tumors accompanied by angiogenesis), and the underlying structure 1203x may receive the transmitted ultrasound signal 1201s.

A delay time 1208 to be identified is a delay time between a position of the first pulse (an RF signal 1204 in (b) of FIG. 12) and a position of the second pulse (an RF signal 1205).

Here, the first pulse is a pulse before displacement 1207 of the underlying structure 1203x, in the received ultrasound signal 1201s.

The second pulse is a pulse after the displacement 1207 of the object to be measured.

Then, the displacement 1207 is determined based on the identified delay time 1208.

Then, it is possible to determine whether movement of the underlying structure 1203x with the size of the displacement 1207 is predetermined movement.

The underlying structure 1203x may be determined as malignant tumors (cancer) when the movement is determined to be the predetermined movement, and the underlying structure 1203x may be determined as benign tumors or normal tissue when the movement is determined not to be the predetermined movement.

Such determination of cancer may be made by, for example, the convergence control unit 1X7 (FIG. 13).

More specifically, the displacement estimating apparatus may perform processing with a larger window size at the n-th round, as the correlation value identified at the (n−1)th round is larger, which will be described later in detail.

The process using the window size may be, for example, a process of calculating the correlation value at the n-th round, using data of a window portion of the window size in the received ultrasound signal 1201s.

Since an appropriate window according to a signal level of an ultrasound reception signal is set at each round, it is possible to increase the accuracy of the convergence, guide the convergence with a small number of iterations, and estimate displacement with less processing amount and high accuracy.

The following embodiment is merely illustrative for the principles of various inventive steps.

It is understood that variations of the details described herein will be apparent to others skilled in the art.

It's the intent, therefore, to be limited only by the scope of the patent claims, and not by the specific, illustrative details herein.

FIG. 1 illustrates a displacement estimation method.

The main embodiment of the present invention is illustrated in FIG. 1.

RFSig(d,l,f) denotes RF signals obtained from an ultrasound unit, wherein d represents a depth direction (a direction 81D in FIG. 8), l represents a line direction (the direction 81L), and f denotes the frame direction (a direction 81F).

Figure 8:
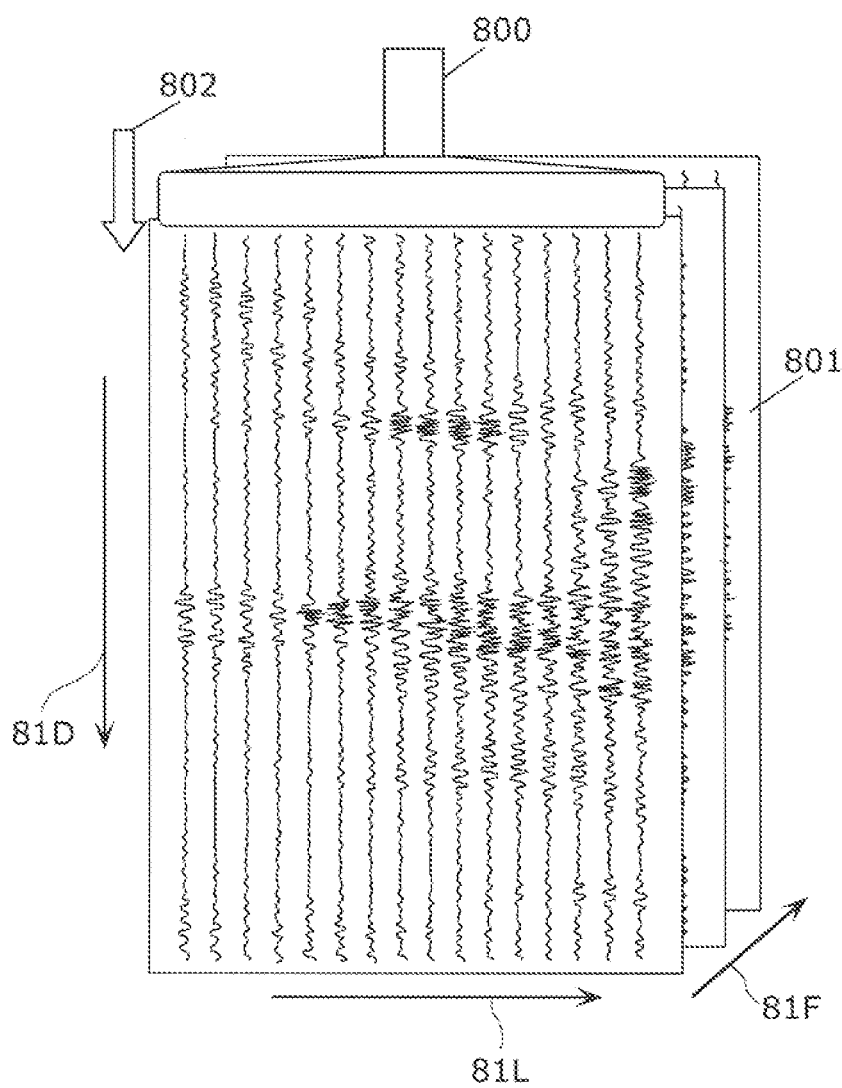
FIG. 8 illustrates ultrasound RF signals.

It is further illustrated in FIG. 8.

One line in one frame of such RF signals (depicted by 801) is generated by a mechanism in which an ultrasound transducer 800 transmits a pulse toward a scan direction (a direction 802) at the location of the line.

Here, the pulse interacts with underlying structures along its path through reflections and scattering, and the ultrasound transducer 800 receives the reflected and scattered signal.

The signal is converted by the ultrasound unit to the corresponding line.

Multiple lines are generated using the same mechanism but at different locations, and multiple frames are generated at different time instances.

In FIG. 12, (a) illustrates displacements of underlying structure, and (b) illustrates the effects on RF signals.

The mechanism by which displacements of the underlying structures in the scanned medium are reflected as delays in the RE signals is illustrated in FIG. 12.

For illustrative purpose, it is assumed that one pulse in one line is transmitted, and it is assumed that there is only one reflective boundary at the underlying structure.

At the first time instance (see the left portion of (a)), the ultrasound transducer 1200 transmits a pulse (1201) toward the scanned medium.

This pulse propagates through the medium until it reaches the reflective boundary of the underlying structure 1203 (1203x).

This boundary causes the pulse to reflect back toward the transducer (see reflected pulse 1202).

The transducer receives the pulse and converts it to the RF signal 1204 (the top portion in (b) of FIG. 12).

The location of the pulse in the whole RF signal 1204 depicts the time that the transmitted pulse 1201 needs to travel toward the underlying structure 1203 and reflect back.

In the second time instance (see the right portion of (a) in FIG. 12), the RF signal 1205 (the bottom portion in (b) of FIG. 12) is created in the same mechanism, but the underlying structure is displaced to a new position (see an underlying structure 1206 after the displacement).

Displacement x (displacement 1207) causes the transmitted pulse (the pulse 1201) to take a longer time to propagate and reflect at the boundary of the underlying structure, resulting in a delay in the RF signals (see the identified delay time 1208).

In this example, the direction of the displacement x is a direction 1203d in FIG. 12.

Knowing this delay value 1208, the displacement (displacement 1207) can be deduced.

In a medium with multiple underlying structures, multiple reflected pulses are generated.

Each underlying structure displaces by a different amount, causing the delays for the reflected pulses in RF signals to be different.

These pulses overlap and interact, which makes it difficult to estimate the exact displacement of each underlying structure.

The present invention presents a method to accurately estimate the displacements of the underlying structures by iterative estimation.

According to the main embodiment as shown in FIG. 1, the present invention includes the following main blocks.

More specifically, a displacement estimating apparatus includes an RF signal warping unit 100 (FIG. 5), a displacement estimation unit 101 (FIG. 9), a window calculation unit 102 (FIG. 2), a convergence guide unit 103 (FIG. 7), and an output switch 104.

The RF signal warping unit 100 warps selected lines in selected frames of RF signals for the current estimation round (the n-th round) based on the displacement estimation results dispRound(d,l,round) of the previous estimation rounds (the (n−1)th round).

The selected lines are set to zero for the first round.

The output of this block is the warped RF signals for an estimation round RFSigWarp(d,l,f,round).

It should be noted that for the first estimation round (i.e. round=1), RFSigWarp(d,l,f,1) and RFSig(d,l,f) that is the RF signal obtained from the ultrasound unit are identical due to the initialization of dispRound(d,l,0) to zero.

For estimating displacements, a predefined set of frames can be chosen as the input for this block.

For the purpose of illustration, two frames are chosen, denoted by $f_1$ and $f_2$.

The purpose of RF signal warping is to modify one RF signal to match the other based on the estimated displacements in the previous round.

Then, the residue displacements are estimated from the modified RF signals and added to the displacements in the previous round to create the new displacements.

After a certain (predetermined) number of estimation rounds, the estimated displacements produce a good match of modified RF signals, and the residue displacements converge to zero.

The displacement estimation unit 101 estimates displacements from the RF signals RFSigWarp(d,l,f,round) as a derivation of time delay in the RF signals.

A preferred method to perform this task is, but not limited to, autocorrelation, with the estimation windows at each depth described by winStart(d,l) and winEnd(d,l).

The window calculation unit 102 calculates the estimation window parameters winStart(d,l) and winEnd(d,l) for the selected lines at each depth.

The window calculation unit 102 takes the RF signals RFSigWarp(d,l,f,round), the current round number curRound, and the RF signal difference residue(d,l,round) from the convergence guide unit 103 as the inputs.

The convergence guide unit 103 performs the process of guiding the convergence according to a technique of the present invention.

In other words, the difference between the warped RF signals is calculated to determine the quality of the estimated displacements.

The round (including the current round) at which this difference is smallest is determined to represent the most accurate displacement estimation result.

The output of this block is the current estimation round number curRound, the round number at which the RF signal difference is smallest, minResidueRound(d,l), and the RF signal difference residue(d,l,round) as a measure of the quality of the estimated displacements.

Smaller residue(d,l,round) indicates better quality, and reduction of residue(d,l,round) across estimation rounds indicates convergence.

Possible methods to calculate the difference between the warped RF signals are, but not limited to, 'sum of squared differences' and 'absolute difference'.

The output switch 104 takes curRound and minResidueRound(d,l) as inputs.

If the current round number reaches a maximum value, the most accurate estimation result is chosen as the final output.

Otherwise, it is chosen as the input of the RF signal warping unit 100 for the subsequent estimation round, and residue (d,l,round) and curRound are passed to the displacement estimation unit 101 as inputs.

The following paragraphs present several detailed embodiments based on the main embodiment as shown in FIG. 1.

Figure 5:
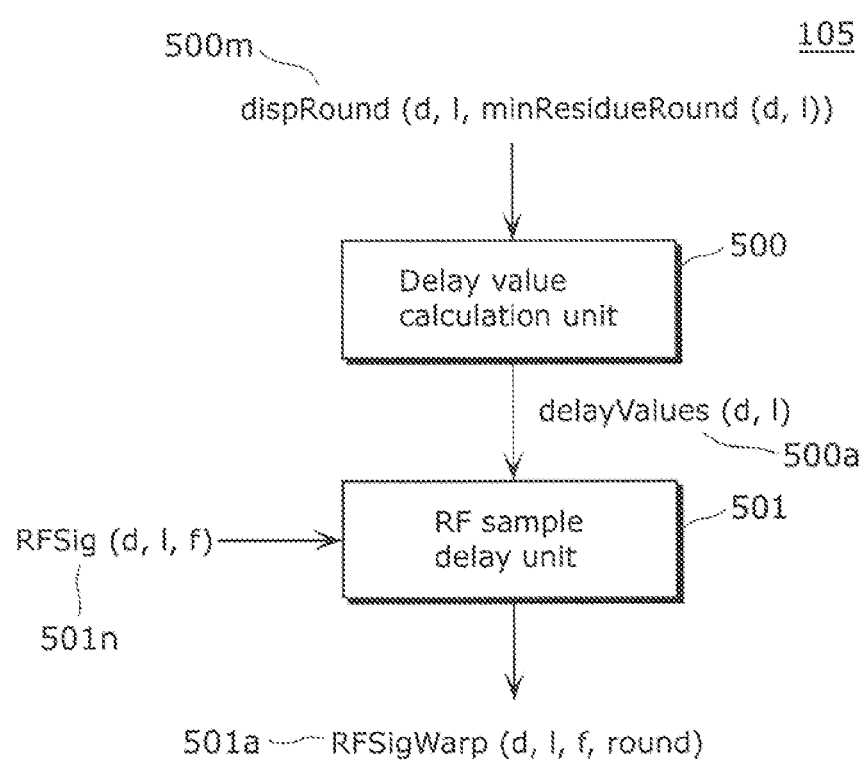
FIG. 5 illustrates an RF signal warping method according to the present invention.

FIG. 5 illustrates an RF signal warping method.

As a detailed embodiment of this invention, the RF signal warping unit 100 of the main embodiment is realized with the method depicted by FIG. 5.

Displacements result in shifting and stretching of RF signals.

Thus, a delay value calculation unit 500 calculates the delay values (the delay time 1208) in samples that make RFSig(d,l,$f_1$) match RFSig(d,l,$f_2$) from the most accurate displacement estimation result of the previous rounds dispRound(d,l,minResidueRound(d,l)) as the following formula.

$$delayValues(d, l) = \frac{dispRound(d, l, minResidueRound(d, l)) \times 2 \times fs}{c} \quad \text{[Math. 1]}$$

Here, fs is the sampling frequency of the RF signals, and c is the speed of sound in the scanned medium.

Displacements in the scanned medium are reflected as delays in the resulted RF signals.

Knowing the delay value at each depth, all the samples (corresponding to all depths) in each line in either RFSig(d,l,$f_1$) or RFSig(d,l,$f_2$) can be delayed accordingly to match the other.

This is performed by an RF sample delay unit 501.

In one embodiment, the RF sample delay unit 501 performs the delay with the aid of signal interpolation.

In an alternative embodiment, the RF sample delay unit 501 performs the delay with the aid of a fractional delay filter.

Figure 6:
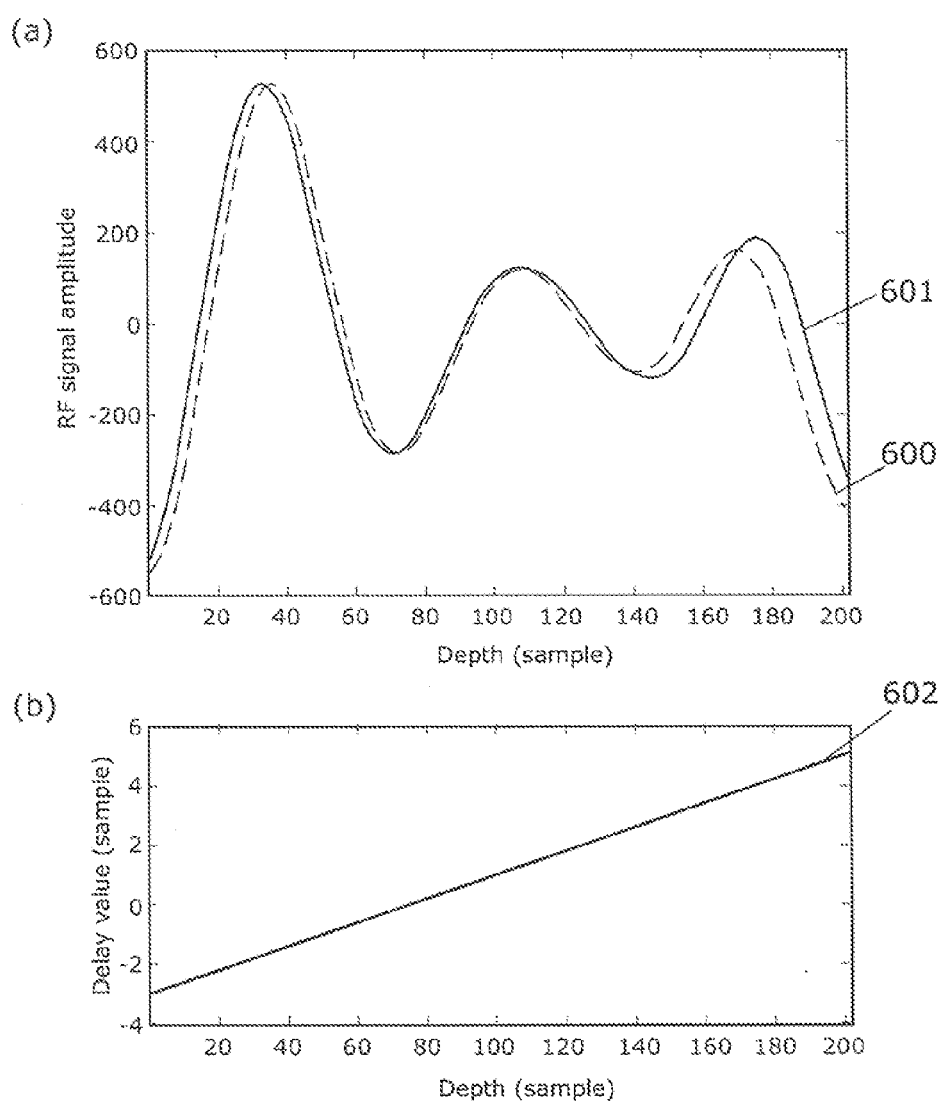
FIG. 6 illustrates RF signal warping and RF sample delay.

FIG. 6 illustrates RF signal warping and RF sample delay.

The RF signal warping process is illustrated in FIG. 6.

It's established in FIG. 12 that displacements cause delays in RF signals.

The purpose of RF signal warping is to reverse this effect by introducing delays for one RF signal in the opposite direction with respect to the estimated displacements.

The expected result of this reversion is that the warped RF signals match one another.

delayValues(d,l) calculated by the delay value calculation unit 500 represents the values by which each sample in one RF signal is delayed to achieve the matching.

Two RF signals 600 and 601 are used for this illustration (FIG. 6).

Data 602 indicates the delayValues(d,l) calculated by the delay value calculation unit 500 after a round of estimation.

It can be observed that a value at a specific depth in delayValues(d,l) represents the amount with which the sample at the same depth in the RF signal 600 needs to be delayed in accordance with the delay value calculation unit 601.

However, the delay values in delayValues(d,l) are not always integers.

Therefore, to be able to delay each sample in the RF signal 600 according to delayValues(d,l), the signal interpolation or fractional delay filter are two possible choices.

The displacement estimation unit 101 is applied to the RF signals to obtain the displacements for the first round, the residue displacements for the subsequent round, and combines them to obtain the final displacements.

Figure 9:
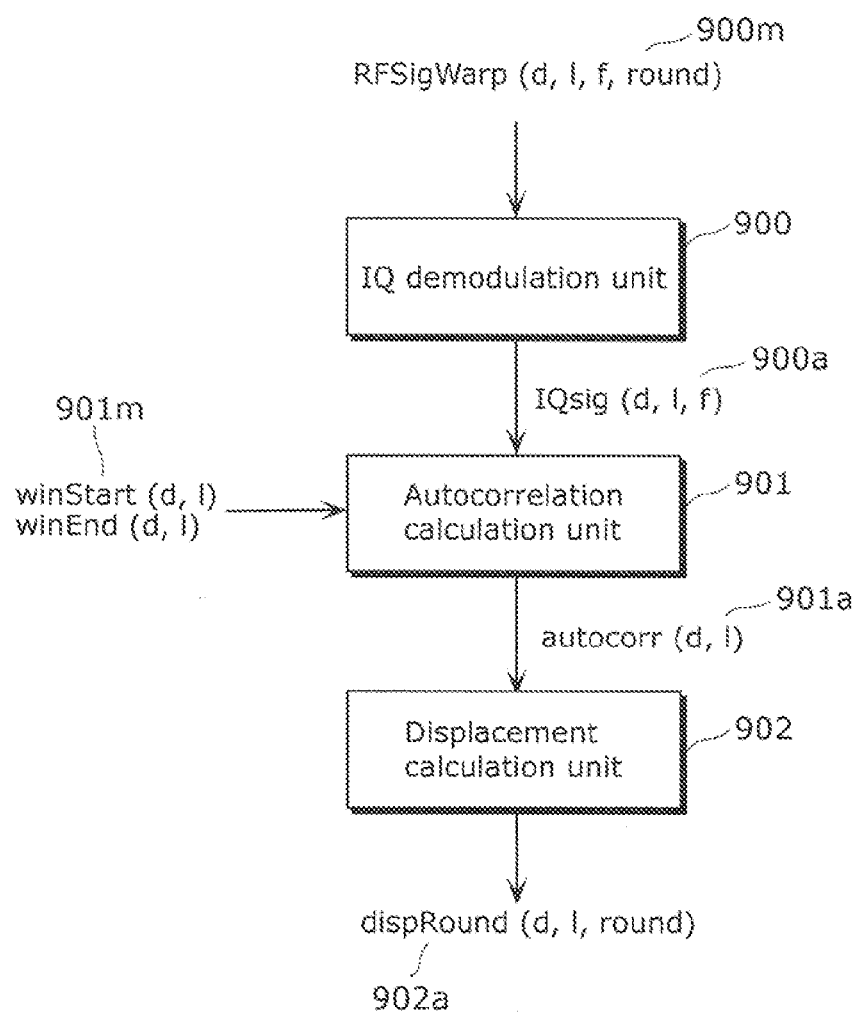
FIG. 9 illustrates a displacement estimation using autocorrelation.
Figure 10:
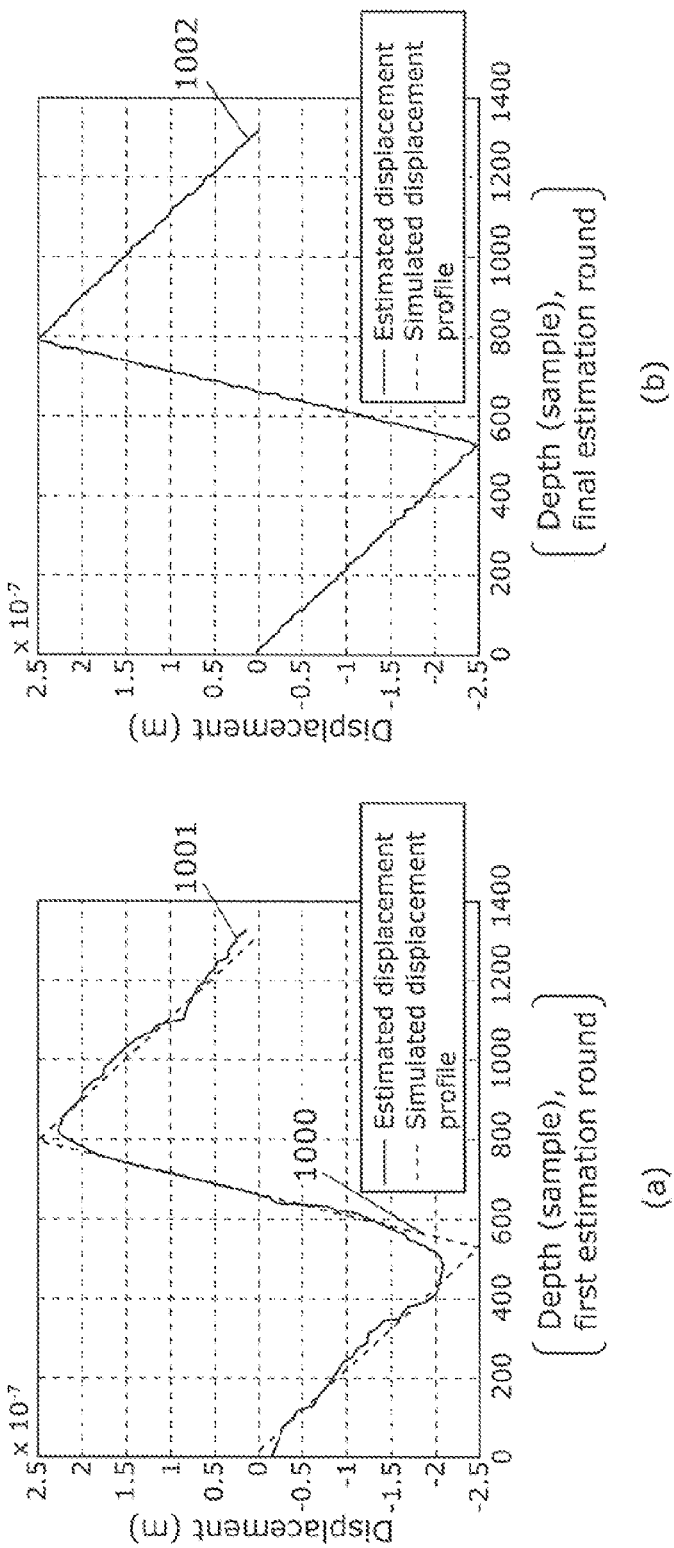
FIG. 10 illustrates an example of displacement estimation results using the present invention in simulation.
Figure 11:
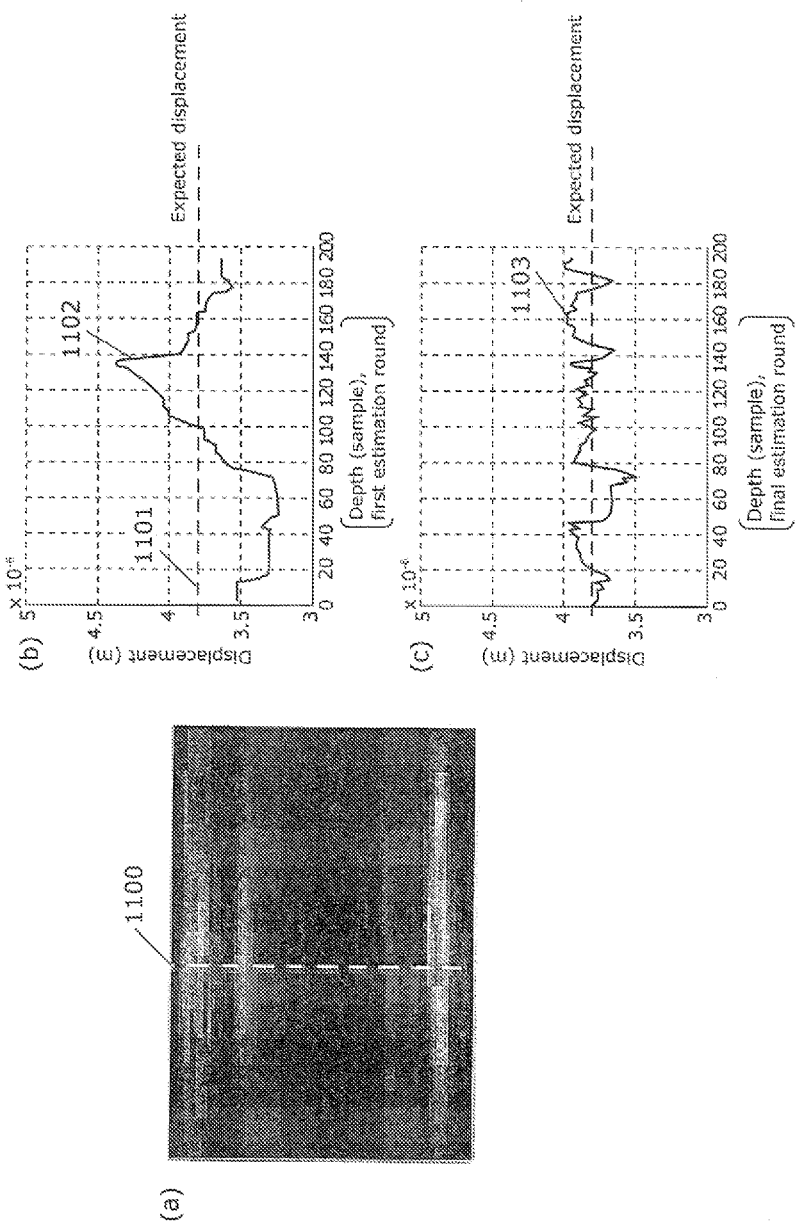
FIG. 11 illustrates an example of displacement estimation results using the present invention in a phantom experiment.

A preferred embodiment is depicted in, but not limited to, FIG. 9.

FIG. 9 illustrates a displacement estimation using autocorrelation.

An IQ demodulation unit 900 converts the RF signals RFSigWarp(d,l,f,round) to base-band signals IQSig(d,l,f).

An autocorrelation calculation unit 901 calculates autocorr (d,l) according to the following formula.

$$autocorr(d, l) = \sum_{l_i=winStart(d,l)}^{winEnd(d,l)} IQSig(d, l_i, f_1) \times conj(IQSig(d, l_i, f_2)) \quad \text{[Math. 2]}$$

Here, conj( ) represents the conjugation operation.

Finally, a displacement calculation unit 902 converts autocorr(d,l) to displacements according to the following formulae.

$$residueDisp = \frac{\lambda}{4\pi}\arg(autocorr(d, l))$$ [Math. 3]

$$dispRound(d, l, \text{round}) =$$

$$dispRound(d, l, \text{round} - 1) + residueDisp$$

Here, arg( ) is the function to calculate the argument of complex numbers.

With round starting from 1 (representing the first round), dispRound(d,l,0) is initialized to zero.

Figure 2:
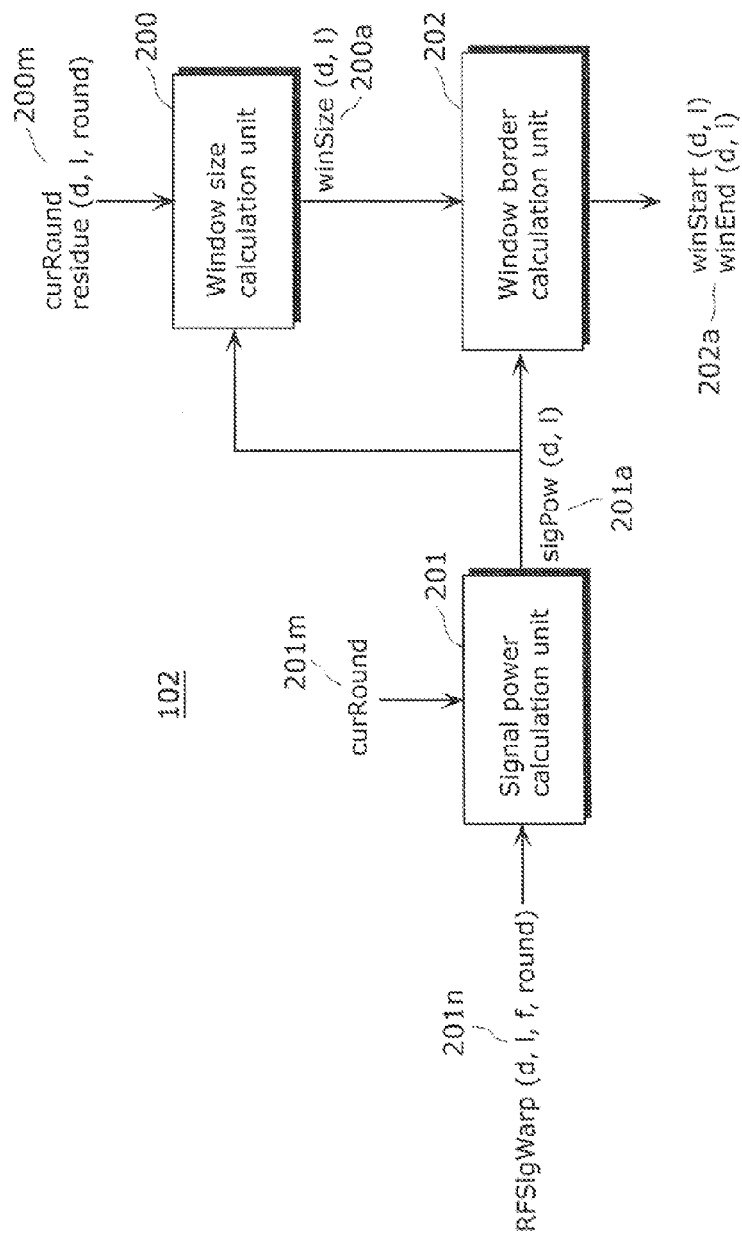
FIG. 2 illustrates a window calculation method according to the present invention.

FIG. 2 illustrates a window calculation method.

The window calculation unit 102 decides the estimation windows differently for each depth of each line in each estimation round.

It is depicted in FIG. 2.

FIG. 3 illustrates a specific example of the window size calculation.

A window size calculation unit 200 determines the window size for each estimation round.

The output of this block is winSize(d,l).

In the preferred embodiment, the window sizes for each round are varied as decreasing functions of round.

This is illustrated in FIG. 3.

In an embodiment of the window size calculation unit 200 (FIG. 2), the window size is directly related to the estimation round number by a decreasing function winSizeRound (round), as in FIG. 3(*a*).

For the current estimation round specified by curRound, the window size is specified for all depths based on the following formula.

winSize(*d,l*)=winSizeRound(curRound) for all *d* and *l*

'Fixed windowing scheme' denotes the process of choosing the same value of winSize(d,l) to be the estimation window size at all depths for displacement estimation.

The advantage of 'fixed windowing scheme' is that it does not require high computational load (requires relatively low computational load), and it is suitable for cases wherein the RF signal energy is distributed regularly along the depth direction.

In an alternative embodiment of the window size calculation unit 200, the window size at each depth is calculated based on an upper limit maxWin(round), a lower limit minWin(round), and the RF signal power sigPow(d,l).

maxWin(round) and minWin(round) are decreasing functions of round.

This is illustrated in FIG. 3(*b*), denoted 'instantaneous power windowing scheme'.

The following condition is applied.

winSize(*d,l*)∈[minWin(curRound),maxWin(curRound)]  [Math. 4]

Additionally, winSize(d,l) can also be inversely proportional to sigPow(d,l), i.e. the maximum window size corresponding to sigPow=0, and the minimum window size corresponding to maximum sigPow, as depicted in FIG. 3(*b*).

Although requiring a higher computational load comparing to 'fixed windowing scheme', 'instantaneous power windowing scheme' is more accurate, especially for cases wherein the RF signal energy is highly uneven along the depth direction.

A larger estimation window is specified for regions with low signal power to overcome a low signal-to-noise ratio, and a smaller estimation window is specified for regions with large signal power to obtain a more detailed displacement distribution.

Nevertheless, for RF signals with regular distribution of signal energy, 'fixed windowing scheme' and 'instantaneous power windowing scheme' are comparable.

In an alternative embodiment of the window size calculation unit 200, the window sizes at all depths can be calculated so that the signal energies in all windows remain equal, denoted 'constant energy windowing scheme'

A signal power calculation unit 201 (FIG. 2) calculates the average power of the RF signals along the frame direction.

The signal power calculation unit 201 takes the warped RF signals RFSigWarp(d,l,f,round) and the current round number curRound as inputs.

There are multiple frames in RFSigWarp(d,l,f,curRound), and the power is calculated as the following formula.

$$sigPow(d, l) = \frac{1}{N}\sum_{i=1}^{N}(RFSigWarp(d, l, f_i, curRound))^2$$ [Math. 5]

N is the total number of frames chosen for the calculation.

FIG. 4 illustrates an example of a symmetrical window and an energy equalized window.

A window border calculation unit 202 (FIG. 2) calculates the window borders at each depth for each line.

The example is illustrated in FIG. 4.

In an embodiment of the window border calculation unit 202, winSize(d,l) calculated by the window size calculation unit 200 is the input, and winStart(d,l) and winEnd(d,l) are calculated so that the windows are symmetrical with respect to the corresponding depths (denoted 'symmetrical window'), according to the following formulae.

$$winStart(d, l) = d - \text{ROUND}\left(\frac{winSize(d, l)}{2}\right)$$ [Math. 6]

$$winEnd(d, l) = d + \text{ROUND}\left(\frac{winSize(d, l)}{2}\right)$$

ROUND( ) denotes the process of rounding to the nearest integer.

The process is illustrated in FIG. 4(*a*).

The advantage of symmetrical window is that it does not require high computational load.

It is suitable for cases wherein RF signal power does not abruptly change from sample to sample in the depth direction.

In an alternative embodiment of the window border calculation unit 202 is as follows.

Here, winSize(d,l) calculated by the window size calculation unit 200 is the input.

Next, winStart(d,l) and winEnd(d,l) are calculated so that the signal energies on both sides of each depth are equal (denoted 'energy equalized window'), by the following formulae.

$$\sum_{d_i=winStart(d,l)}^{d}sigPow(d_i, l) = \sum_{d_i=d}^{winEnd(d,l)}sigPow(d_i, l)$$ [Math. 7]

$$winEnd(d, l) - winStart(d, l) + 1 = winSize(d, l)$$

The process is illustrated in FIG. 4(*b*).

Although requiring a higher computational load comparing to 'symmetrical window', 'energy equalized window' can suppress the effect of uneven distribution of signal power along the depth direction, which causes bias in the conventional windowing technique.

Figure 7:
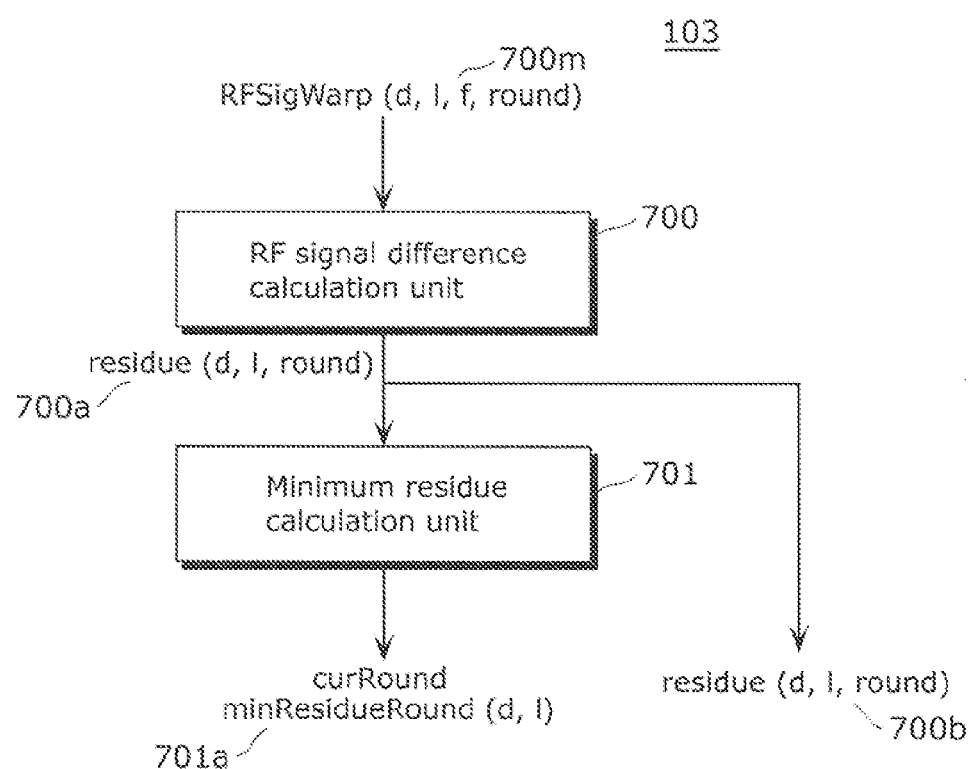
FIG. 7 illustrates a convergence guide method according to the present invention.

FIG. 7 illustrates a convergence guide method.

The convergence guide unit 103 in FIG. 1 makes sure that the method described in the present invention enables convergence.

The convergence guide unit 103 takes the warped RF signals RFSigWarp(d,l,f,round) as the input, as depicted in FIG. 7.

An RF signal difference calculation unit 700 calculates the difference between the warped RF signals, and outputs the difference in each estimation round as residue(d,l,round) for each depth in each line.

As the main purpose of the RF signal warping unit 100 is to modify one of the RF signals to match the other, this difference residue(d,l,round) is a measure of how closely the RF signals are matched.

For a specific estimation round (specified by round), in order to evaluate the quality of estimated displacement dispRound(d,l,round), the RF signal warping unit 100 takes dispRound(d,l,round) as the input.

With this, the difference between the warped RF signals is calculated to evaluate the level of matching.

These warped signals are also used as the input for displacement estimation of the subsequent round, hence they are denoted as RFSigWarp(d,l,f,round+1).

Thus, residue(d,l,round) is calculated from RFSigWarp(d,l,f,round+1).

An example of the calculation conducted by the RF signal difference calculation unit 700 (FIG. 7) is, but not limited to, the following formula (namely, sum of squared differences).

$$\text{residue}(d, l, \text{round}) = \sum_{all d_i} (RFSigWarp(d_i, l, f, \text{round} + 1) - FSigWarp(d_i, l, f_2, \text{round} + 1))^2 \quad [\text{Math. 8}]$$

Here, $f_1$ and $f_2$ represent the two frames chosen for estimation.

In this example, the same signal difference value is specified for all depths in one line, representing the global matching of RF signals for the corresponding line.

'Sum of squared differences' is suitable when displacements do not just occur in a small area, so iteration for the whole lines takes place.

Another example of the calculation conducted by the RF signal difference calculation unit 700 (FIG. 7) is, but not limited to, the following formula (namely, absolute difference).

$$\text{residue}(d,l,\text{round})=|RFSigWarp(d,l,f_1,\text{round}+1)-RFSigWarp(d,l,f_2,\text{round}+1)| \quad [\text{Math. 9}]$$

Here, $f_1$ and $f_2$ represent the two frames chosen for estimation.

In this example, each depth in each line has an individual value of a signal difference, representing the local matching of RF signals.

'Absolute difference' is suitable for cases whereby displacements occur only in a small region in a depth direction, so that local iteration within that region can take place.

A minimum residue calculation unit 701 checks, for each depth and line in residue(d,l,round), the round number at which the residue is the smallest based on the following formula.

The formula represents the most accurate estimation results.

$$\text{minResidueRound}(d, l) = \underset{\text{round}}{\arg\min}(\text{residue}(d, l, \text{round})) \quad [\text{Math. 10}]$$

$$\underset{x}{\arg\min}(f(x)) \quad [\text{Math. 11}]$$

The above function returns the value of x that minimizes f(x).

The outputs of the convergence guide unit 103 (FIG. 1) are the current round number curRound, the round number at which the residue is the smallest minResidueRound(d,l), and the signal difference residue(d,l,round).

The output switch 104 (FIG. 1) takes curRound and minResidueRound(d,l) as inputs.

If curRound reaches the maximum value, the output switch 104 chooses the displacement estimation result with the highest accuracy dispRound(d,l,minResidueRound(d,l)) as the final output dispOut.

Otherwise, the displacement estimation of the current round dispRound(d,l,curRound) is replaced with dispRound(d,l,minResidueRound(d,l)) to be used as the input of the RF signal warping unit 100 for the next estimation round.

Hereinafter, the multi-dimensional (two-dimensional or three-dimensional) expansion of displacement estimation will be described.

More specifically, the above embodiment describes a method of calculating one-dimensional displacement in a depth direction of ultrasound.

However, pulsation directions of body tissue, such as blood vessel and tumor tissue, are not limited to the one-dimensional space, and differ depending on a place.

Thus, displacements in directions at a specific position may be calculated by transmitting and receiving ultrasound to and from the directions, and two-dimensional or three-dimensional displacements of tissue may be measured.

With the multi-dimensional measurement, it is expected that the accuracy of diagnosis will be improved.

Examples of a method of transmitting and receiving ultrasound to and from directions include methods, performed by an ultrasound transducer, for changing a direction of a probe using a linear probe one-dimensionally arranged and for transmitting and receiving ultrasound to and from directions through beam forming, using a matrix probe on a two-dimensional array.

When the linear probe is used, the position and the direction of a probe are obtained by tracking the position of the probe using a camera or a position sensor, such as a magnetic sensor, an acceleration sensor, and a gyroscopic compass. Thus, the directions of ultrasound can be determined.

The displacement may be measured in only one direction, such as a depth direction of ultrasound. Furthermore, the displacement may be multi-dimensionally evaluated by decomposing the displacement vector into components in each axial direction of a predetermined two-dimensional or three-dimensional coordinate system.

The depth direction of ultrasound is associated with the predetermined coordinate system by obtaining the position and the direction of a probe using the position sensor and others, because the association between them is necessary for the evaluation.

Hereinafter, the association with strain measurement (elastography) to be applicable to detection of cancer or diagnosis of atherosclerosis (stiffness of blood vessel) will be described as supplemental explanation. The strain is a time derivative of displacement, and is a measure of stiffness of tissue. According to the present invention, the improved accuracy of the displacement estimation will result in the improved accuracy in measurement of the strain. A derivative is used in elastography. In addition, time change waveforms of displacement in a specific portion of tissue can be used to determine tissue properties. For example, it is known that angiogenesis occurs around and within cancer during the growth of the cancer. It is assumed that pulsation of blood vessel or pulsation of the surrounding tissue that is accompanied by the pulsation of blood vessel are temporal change in the displacement. Then, whether or not the pattern and the amplitude of the change are peculiar to cancer may be determined in order to detect the cancer.

Disclosed herein is a displacement estimating apparatus that iteratively estimates displacement using ultrasound signals and includes: a unit configured to transmit, to a medium, at least one of the ultrasound signals to scan the medium; a unit configured to receive the ultrasound signal reflected from the scanned medium; a unit configured to calculate a size of an estimation window; a unit configured to calculate a border of the estimation window based on the calculated estimation window size; an estimating unit configured to estimate displacement for each depth of the ultrasound signal, using the window with the calculated border; a unit configured to warp the ultrasound signal based on the estimated displacement; and a unit configured to guide convergence of a displacement estimating method by calculating a difference between the warped ultrasound signals as the convergence tendency of the method.

Thus, the disclosed method herein includes a method to guide the convergence, a method to overcome factors that limit accuracy, and a method to evaluate the quality of results, and the accuracy of displacement estimation is ensured with a comprehensive iterative approach.

In other words, the following problems will be solved. That is, the prior arts in displacement estimation using ultrasound provide methods to improve the accuracy and resolution of estimation. Some works introduce multiple-stage estimation or iterative estimation. However, the following problems retain: (1) lack of comprehensive iterative approach incorporating methods to guide the convergence of iterative estimation, (2) lack of a quality evaluation method, and (3) lack of a solution for factors that limit the accuracy of displacement. The displacement estimation method according to the present invention solves these problems.

The present invention can be implemented not only as such an apparatus, a system, and an integrated circuit but also as a method using processing units included in the apparatus and others as steps, as a program causing a computer to execute such steps, as a recording medium on which the program is recorded, such as a computer-readable CD-ROM, and as information, data, or a signal indicating the program. Such a program, information, data, or a signal may be distributed via communication networks, such as the Internet.

The present invention is described based on, but not limited to, the embodiments. Without departing from the scope of the present invention, the present invention includes an embodiment with some modifications on the embodiments conceived by a person skilled in the art, and another embodiment obtained through combinations of the constituent elements and steps of the different embodiments in the present invention.

INDUSTRIAL APPLICABILITY

The technique according to the present invention is for introducing a method of estimating displacement using ultrasound signals. It can be used in applications requiring estimation of displacements, either as the final results or as the intermediate step for further processing. It can be deployed in medical and industrial ultrasound machines.

The present invention can thus provide a displacement estimating apparatus that can estimate displacement with high accuracy, and that can provide information appropriate for differentiating benign tumors from malignant ones, or normal tissue, based on the estimated displacement.

REFERENCE SIGNS LIST

1X Displacement estimating apparatus
1X1 Transmission unit
1X2 Receiving unit
1X3 Size calculating unit
1X4 Border calculating unit
1X5 Estimating unit
1X6 Warping unit
1X7 Convergence control unit
1201$s$ Ultrasound signal
1203$x$ Underlying structure
1X3M Window size
1X4M Border information
1XbM Displacement
1X7M Correlation value
100 RF signal warping unit
103 Convergence guide unit
101 Displacement estimation unit
102 Window calculation unit
103 Convergence guide unit
104 Output switch
600, 1204, 1205 RF signal
800, 1200 Ultrasound transducer
1200M Medium
1208 Delay time
100$a$, 101$a$, 1021$a$, 103$a$, 104$a$, 104$b$, 104$c$ Information
201$n$, 201$m$, 201$a$, 200$m$, 200$a$, 202$a$ Information
500$m$, 500$a$, 501$n$, 501$a$ Information
700$m$, 700$a$, 701$a$, 700$b$ Information
900$m$, 900$a$, 901$m$, 901$a$, 902$a$ Information

The invention claimed is:

1. A displacement estimating method of iteratively estimating displacement using ultrasound signals, said method comprising:
transmitting, to a medium, at least one of the ultrasound signals to scan the medium;
receiving the ultrasound signal reflected from the scanned medium;
calculating a size of a window;
calculating a border of the window based on the calculated window size;
estimating displacement for each depth of the ultrasound signal, using the window with the calculated border;
warping the ultrasound signal based on the estimated displacement; and
guiding convergence of said method using the warped ultrasound signal so that a correlation value of the ultrasound signal is larger;
wherein the window size is calculated so that signal energies in all windows are equal.

2. The displacement estimating method according to claim 1, wherein the calculated window size for consecutive rounds is varied in a gradually reducing manner.

3. The displacement estimating method according to claim 1, further comprising:
varying upper and lower limits of the window size for consecutive rounds in a gradually reducing manner; and
calculating a window size between the upper and lower limits as the window size at each of the depths, based on signal power at the depth.

4. The displacement estimating method according to claim 1,
wherein the window size is calculated inversely with the correlation value of the ultrasound signal.

5. The displacement estimating method according to claim 1,
wherein the window with the border is extended to both sides of a corresponding one of the depths so that the window is symmetrical with respect to the depth.

6. The displacement estimating method according to claim 1, further comprising
warping the ultrasound signal by delaying each sample in the ultrasound signal by a calculated delay value.

7. The displacement estimating method according to claim 1, further comprising:
calculating an absolute value or a square of a signal difference between warped RF signals after each round; and
determining one of the rounds at which the calculated signal difference is smallest.

8. A displacement estimating method of iteratively estimating displacement using ultrasound signals, said method comprising:
transmitting, to a medium, at least one of the ultrasound signals to scan the medium;
receiving the ultrasound signal reflected from the scanned medium;
calculating a size of a window;
calculating a border of the window based on the calculated window size;
estimating displacement for each depth of the ultrasound signal, using the window with the calculated border;
warping the ultrasound signal based on the estimated displacement; and
guiding convergence of said method using the warped ultrasound signal so that a correlation value of the ultrasound signal is larger;
wherein the window with the border is extended to both sides of a corresponding one of the depths so that signal energies on both sides of the window are equal at the depth.

9. A displacement estimating apparatus that iteratively estimates displacement using ultrasound signals, said apparatus comprising:
a transmission unit configured to transmit, to a medium, at least one of the ultrasound signals to scan the medium;
a receiving unit configured to receive the ultrasound signal reflected from the scanned medium;
a size calculating unit configured to calculate a size of a window so that signal energies in all windows are equal;
a border calculating unit configured to calculate a border of the window based on the calculated window size;
an estimating unit configured to estimate displacement for each depth of the ultrasound signal, using the window with the calculated border;
a warping unit configured to warp the ultrasound signal based on the estimated displacement; and
a convergence control unit configured to guide convergence of a displacement estimating method performed by said displacement estimating apparatus, using the warped ultrasound signal so that a correlation value of the ultrasound signal is larger.

* * * * *